Figure 1:
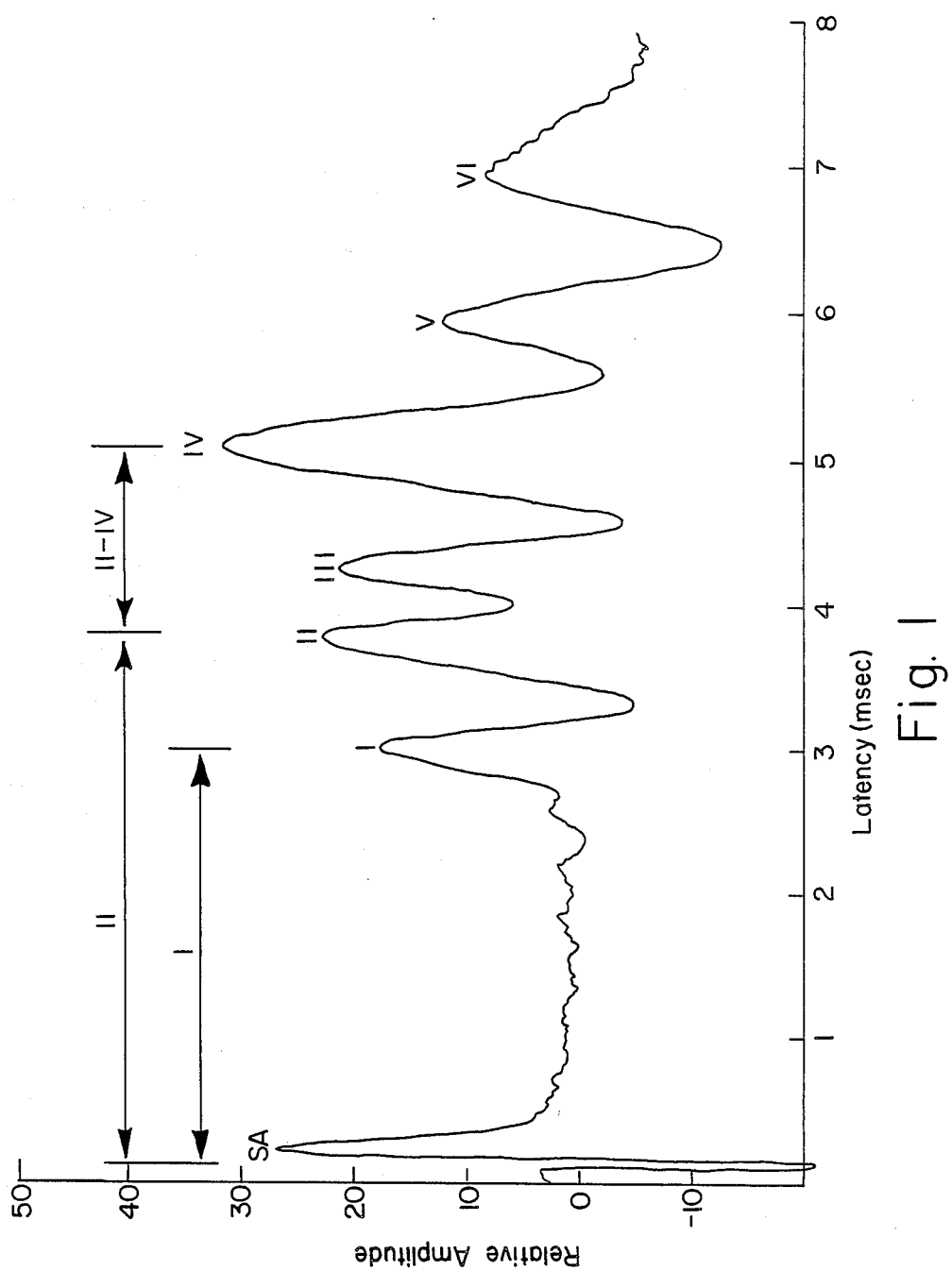

United States Patent [19]

Notvest

[11] Patent Number: 4,783,486

[45] Date of Patent: Nov. 8, 1988

[54] TOLRESTAT FOR HEARING IMPAIRMENT

[75] Inventor: Ronald R. Notvest, Woodbrige Middlesex, N.J.

[73] Assignee: American Home Products Corporation, New York, N.Y.

[21] Appl. No.: 4,007

[22] Filed: Jan. 16, 1987

[51] Int. Cl.⁴ .......................................... A61K 31/195
[52] U.S. Cl. .................................................. 514/562
[58] Field of Search ....................................... 514/562

[56] References Cited

U.S. PATENT DOCUMENTS 4,568,693 2/1986 Sestans ................................. 514/524

OTHER PUBLICATIONS

Notvest et al.–Fed. Proc. 45, No. 3; 463, 1986.
Novest et al.–Fed. Proc., 45:462, 1986.
Cecil–Textbook of Medicine, W. B. Saunders Co., 1982.

*Primary Examiner*—Frederick E. Waddell
*Attorney, Agent, or Firm*—John W. Routh

[57] ABSTRACT

A method is disclosed for improving hearing by alleviating auditory nerve dysfunction by administering an effective amount of tolrestat.

5 Claims, 2 Drawing Sheets

TOLRESTAT FOR HEARING IMPAIRMENT

BACKGROUND OF THE INVENTION (a) Field of the Invention

This invention relates to a novel therapeutic use of N-[[5-(trifluoromethyl)-6-methoxyl-1-naphthenyl]-thioxomethyl]-N-me More specifically this invention relates to a method for improving a hearing deficiency in diabetic humans.

(b) Prior Art

The active agent of this invention, N-[[5-(trifluoromethyl)-6-methoxy-1-naphthenyl]-thioxomethyl]-N-methylglycine or a therapeutically acceptable salt thereof, is disclosed in U.S. Pat. No. 4,568,693, issued Feb. 4, 1986. This active agent, hereinafter designated by its generic name tolrestat, previously has been reported to be useful in preventing or relieving diabetic complications such as cataracts, neuropathy, nephropathy and retinopathy (See U.S. Pat. No. 4,568,693). We have now found unexpectedly that tolrestat, either in its free acid form or in its therapeutically acceptable salt form, is useful for improving a hearing deficiency in humans suffering from diabetes mellitus.

This finding, coupled with the fact that tolrestat is a relatively safe drug, renders the method of this invention particularly useful and advantageous.

SUMMARY OF THE INVENTION

According to this invention a method is provided for improving a hearing deficiency in a diabetic human in need of said treatment, which comprises administering to the human an effective amount of tolrestat, or a therapeutically acceptable salt thereof.

DETAILS OF THE INVENTION

According to the present method, tolrestat, either in its free acid form or in the therapeutically acceptable salt form, is employed as the active agent. Examples of suitable salt forms are described in U.S. Pat. No. 4,568,693 and include the sodium, potassium, magnesium triethylamine and benzylamine salt forms. A preferred salt form is the sodium salt, i.e. tolrestat sodium.

Tolrestat or a therapeutically acceptable addition salt thereof is administered to humans suffering from hearing impairment caused by auditory nerve dysfunction, either orally or parenterally. For many reasons oral administration is preferred.

While tolrestat or a therapeutivally acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 4,568,693, herein incorporated by reference in its entirety.

When utilizing tolrestat or one of its above-noted salts as agents for alleviating auditory nerve dysfunction, the total dose of active agent can range from 0.1 to 20 mg per kilogram of body weight per day with a preferred dosage range of from 50 to 400 milligrams per day. Generally, a parenteral dose or an oral dose is administered in one to four applications per day. Such doses are considered to be an effective amount when, following their administration, improved hearing is experienced by the patient, or when the subjective symptoms complained of by said human beings are reported as having disappeared, or being ameliorated or reduced in severity following such treatment.

The effectiveness of tolrestat or its therapeutically acceptable salts as agents for alleviating auditory nerve dysfunction has been demonstrated in animals.

EXAMPLE I

MATERIAL AND METHODS

Sprague-Dawley male rats (Charles Riber Breeding Laboratories Wilmington, MA) weighing between 200 to 250 grams were anesthetized (pentobartibal 50 mg/kg i.p.) and implanted with cortical electrodes. Following recovery from anesthesia, animals were housed in individual cages with free access to water and food.

In the following portion of this example, ABR means auditory evoked brainstem response and STZ stands for streptozotocin.

Binaural, open-field auditory-evoked brainstem responses were elicited by 512 repetitive audible clicks (0.01 msec duration square wave, 2 Hz, 64 dB) delivered by a speaker 60 cm above the rat. The electrical signal was differentially amplified (low pass filter 300 Hz; high pass filter 3000 Hz) and averaged with a digital oscilloscope. The digitized signal was then stored on a floppy disk. Latencies for all peaks were determined by recalling the ABR records from disk and visually selecting the center of the peak with the aid of an electronically controlled cursor. All records were read blindly by an individual who had previous experience reading clinical auditory-evoked potentials.

Implanted animals were randomly assigned to one of three equal groups: (1) a vehicle-treated diabetic group, (2) a tolrestat-treated diabetic group, and (3) a vehicle-treated nondiabetic group. Tolrestat-treated rats received vehicle (Tween-80 in distilled water; 2% v/v) containing the equivalent of 20 mg/kg of tolrestant in suspension. Treatment was administered twice daily by gavage for the five-week duration of the study.

Diabetes was chemically induced by the administration of STZ at a dose of 60 mg/kg i.v. one day after recording the prediabetic baseline ABR. The STZ was dissolved in cold 0.03 M citrate buffer, adjusted to a pH of 4.5. Animals assigned to the nondiabetic group received only vehicle.

Plasma glucose levels were determined weekly from blood samples drawn from the tail after a four-hour fast. Glucose levels were quantified by the Abbott A-GENT hexokinase procedure (Abbott Diagnostic Division, 07-9739-F3). The criterion for diabetes was established as a sustained plasma glucose level greater than 300 mg/dl by the second week following induction of diabetes. A one-way analysis of variance was performed on all grouped data.

The data reported in this study for weeks one to three were obtained from 17 nondiabetic controls, 9 vehicle-treated diabetic rats, and 8 tolrestattreated diabetic rats. Prior to the fourth week, one vehicle-treated diabetic rat and one tolrestat-treated diabetic rat died. Data obtained from these two rats were included in the analysis.

The effect of STZ-induced diabetes on the ABR was determined by examining the absolute change in latency from the prediabetic baseline for each week following the induction of diabetes. A two-way analysis of variance was performed on all grouped data, and statistical differences were determined using a Dunnett's one-tail t test. To determine the effect of diabetes on the ABR, within-a-week comparisons were made between the STZ-induced diabetic and nondiabetic groups. The effect of treatment with tolrestat on the diabetesinduced changes of the ABR was determined by comparing differences between tolrestat-treated and vehicle-treated diabetic rats. The statistical significance was considered for probability levels of less than 0.05.

The data from this Example I are summarized in FIGS. 1 and 2 described below:

FIG. 1 shows a typical auditory-evoked brainstem response (ABR) recorded from a conscious rat. Response shown is the average from 512 stimulus presentations triggered off the stimulus artifact (SA). The ABR is labelled by convention as peaks I through VI. Latency measurements used for analysis (peak I and peak II latencies and interpeak latency II-IV) are labelled for reference.

Figure 2:
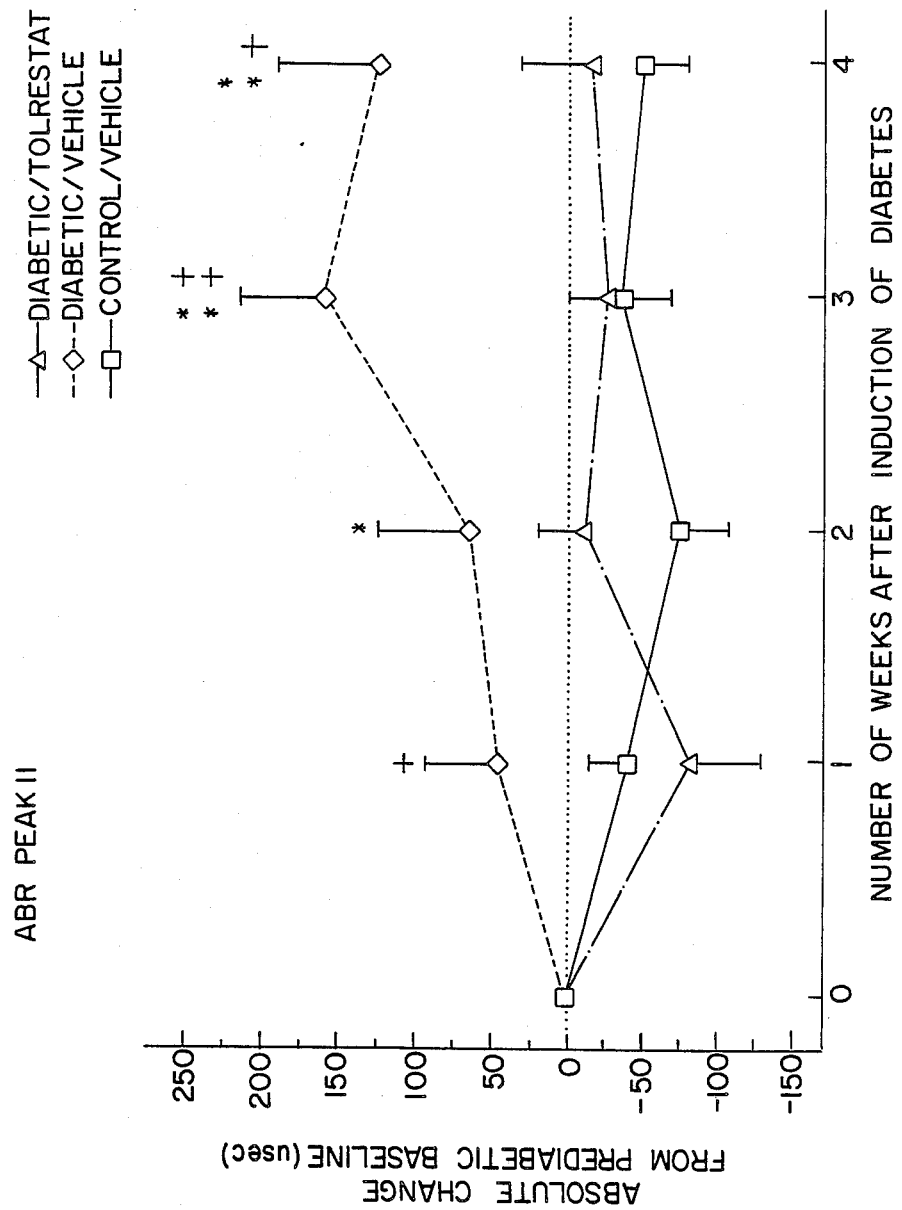

FIG. 2 shows the absolute change in peak II latency of vehicle-treated nondiabetic rats (-) and diabetic rats treated with either vehicle (- - -) or tolrestat (-.-.-). Asterisks identify significant differences between vehicle-treated diabetic rats and controls ($*P<0.05$, $**P<0.01$), while plus signs identify differences between vehicle- and tolrestat-treated diabetic rats ($+P<0.05$, $++P<0.01$). ($\bar{x}\pm$S.E.M.)

Effect of Diabetes and Tolrestat Treatment on the Distal Components of the Auditory Pathway Binaural, open-field ABRs were reproducibly recorded from conscious, unrestrained animals. Typical ABR records had six discrete peaks in the first 8 msec of the recorded response (FIG. 1). The measurements used for analysis included the absolute latencies of peaks I and II, and the interpeak latency between peaks II and IV (FIG. 1).

The effect of STZ-induced diabetes on the distal components of the auditory pathway was initially evaluated by examining the mean absolute changes in peak I latency of the ABR. There was a tendency for the latency of peak I to increase in diabetic rats relative to the control group over the four-week period, although the difference in latencies reached statistical significance only for the second week of diabetes. Diabetic rats treated with tolrestat (one week before and four weeks after the induction of diabetes) had consistently lower peak I latency changes relative to vehicle-treated diabetic rats during the four weeks of diabetes. However, these differences were not statistically significant as compared with those seen in the vehicle-treated diabetic rats.

Because the differences in latency of peak I were not statistically significant, changes in the absolute latency of peak II were examined. Over the four weeks of diabetes, peak II latency increased in diabetic rats relative to the control group (FIG. 2). Statistically significant differences between the peak II ABR latencies of the diabetic and control groups were attained as early as two weeks after the induction of diabetes.

In contrast to vehicle-treated diabetic rats, the diabetic group treated with tolrestat had a decrease in peak II latency relative to its prediabetic baseline. Further, the changes in absolute latency of peak II for the tolrestat-treated diabetic rats were comparable to those of the nondiabetic control group. The differences between the tolrestat-treated diabetic and the vehicle-treated diabetic groups were statistically significant at one, three, and four weeks after the induction of diabetes (FIG. 2).

Effect of Diabetes and Tolrestat Treatment on the Central Transmission Time of the Auditory Pathway The effect of diabetes on the central transmission time of the auditory pathway was evaluated by comparing measurements of the interpeak latency between peaks II and IV of diabetic and control rats. Changes in central transmission time were not significantly different between diabetic and control groups over the four-week period of diabetes. Also, tolrestat had no significant effect on the interpeak latency between peaks II-IV when compared to values obtained from vehicle-treated diabetic rats.

DISCUSSION

These results demonstrate that an early component of the ABR (i.e., the latency to peak II) is delayed in the conscious STZ-induced diabetic rat. The use of the ABR, therefore, represents a novel approach for quantifying slowed nerve transmission in diabetic rats. Further, the procedures used in this study offer an advantage in that the measurements can be made in conscious, unrestrained animals. Consideration of the effect of anesthesia on nerve trasmission or metabolism is not required.

The diabetes-induced slowing of the ABR in the rat is limited to events preceding the occurrence of peak II and does not involve more central tracts of the auditory pathway. Because the slowing occurs between peaks I and II, the results indicate impaired condition in the VIII cranial nerve since it has been suggested that both peak I and peak II are generated by the VIII cranial nerve in rat. Note the article by Edwards, M.S.B., et al., Evoked potentials in rats with misonidazole neurotoxicity. I. Brain stem auditory evoked potentials. J. Neuro-Oncology 1983; 1:115-123. Accordingly, this appears to be the first demonstration that diabetes-induced slowing of nerve conduction may also include cranial nerves.

Results from clinical studies suggest cranial nerve neuropathies may be present in diabetic patients. Specifically, histopathological studies have shown cranial nerve demyelination as well as inner-ear lesions in some diabetic patients. See, for example, an article by Reske-Nielson, E., et al., Pathological changes in the central and peripheral nervous system of young long-term diabetics, Diabetologia 1965; 1:233-241, an article by Makishima, K. and Tanaka, K., Pathological changes of the inner ear and central auditory pathway in diabetics, Ann Otol Rhinol Laryngeal 1971; 80:218-228, and an article by Jorgesen, M.B., Studies on inner-ear function and cranial nerves in diabetes Acta oto-laryng 1961; 53:350-364.

More recently Fedele et al., in an article entitled Impaired auditory brainstem-evoked responses in insulin-dependent diabetic subjects Diabetes 1984; 33:1085-1089 have reported that the latency of peak I of the ABR is delayed in diabetic patients.

These finds complement reports of hearing deficits in diabetic subjects.

Treatment with tolrestat prevented the diabetes-induced delay of the ABR even though the rats remained hyperglycemic. Relevant to these findings are the results of previous studies showing that oral administration of tolrestat decreases the accumulation of intracellular sorbitol in diabetic rats without reducing plasma glucose levels. From in vitro studies it is known that tolrestat inhibits aldose reductase. That tolrestat prevents the deficit in the ABR without affecting the severity of diabetes implies a role for aldose reductase in this cranial nerve neuropathy.

The method of this invention is particularly beneficial for improving hearing by alleviating auditory nerve dysfunction in a diabetic patient suffering from diabetes mellitus.

I claim:

1. A method for improving hearing by alleviating auditory nerve dysfunction in a diabetic human in need of treatment therefore, which comprises administering to the diabetic human an effective amount of tolrestat or a therapeutically acceptable salt thereof.

2. The method of claim 1 in which the effective amount of tolrestat is within the range of from 0.1 to 20 mg per kilogram of body weight.

3. The method of claim 1 in which the effective amount of tolrestat is within the range of 200 to 400 milligrams per day.

4. The method of claim 1 in which the therapeutically acceptable salt is the sodium salt.

5. The method of claim 1 in which the human being treated is suffering from diabetes mellitus

* * * * *